United States Patent [19]

Sakashita et al.

[11] Patent Number: 5,169,397
[45] Date of Patent: Dec. 8, 1992

[54] MEDICAL INSTRUMENT

[75] Inventors: Kiyotoshi Sakashita, Hachioji; Ichiro Kagawa, Akishima, both of Japan

[73] Assignee: Olympus Optical Co., Ltd., Tokyo, Japan

[21] Appl. No.: 648,206

[22] Filed: Jan. 31, 1991

[30] Foreign Application Priority Data

Feb. 8, 1990 [JP] Japan ................................ 2-27072
Nov. 22, 1990 [JP] Japan ................................ 2-318960

[51] Int. Cl.⁵ .................................................. A61B 17/32
[52] U.S. Cl. ...................................... 606/27; 606/185; 606/205; 128/4
[58] Field of Search ................................. 606/37–41, 606/45–50, 27–29; 128/4, 7

[56] References Cited

U.S. PATENT DOCUMENTS

| | | |
|---|---|---|
| 4,060,086 | 11/1977 | Storz . |
| 4,068,667 | 1/1978 | Iglesias . |
| 4,279,245 | 7/1981 | Takagi et al. ............ 128/4 |
| 4,512,343 | 4/1985 | Falk et al. . |
| 4,867,174 | 9/1989 | Skribiski ............ 128/772 |
| 4,905,691 | 3/1990 | Rydell ............ 606/47 |

FOREIGN PATENT DOCUMENTS 60-149616 10/1985 Japan .
63-274908 11/1988 Japan .

OTHER PUBLICATIONS

Article by entitled "New High Polymer Element One Point 10" [Kyoritsu Publisher, High Polymer Gakkai (edition), May 1988 Japan, Naoyuki Koide/Kunisuke, Sakamoto (editors)].

*Primary Examiner*—Peter A. Aschenbrenner
*Attorney, Agent, or Firm*—Frishauf, Holtz, Goodman & Woodward

[57] ABSTRACT

A medical instrument comprises an operating section and an insertion section connected to the operating section and adapted to be inserted into a living body, the insertion section including a tubular member formed of a liquid crystal polymer. The tubular member constituting the insertion section of the medical instrument or a channel tube disposed in the insertion section is formed thin-walled by using the liquid crystal polymer.

11 Claims, 12 Drawing Sheets

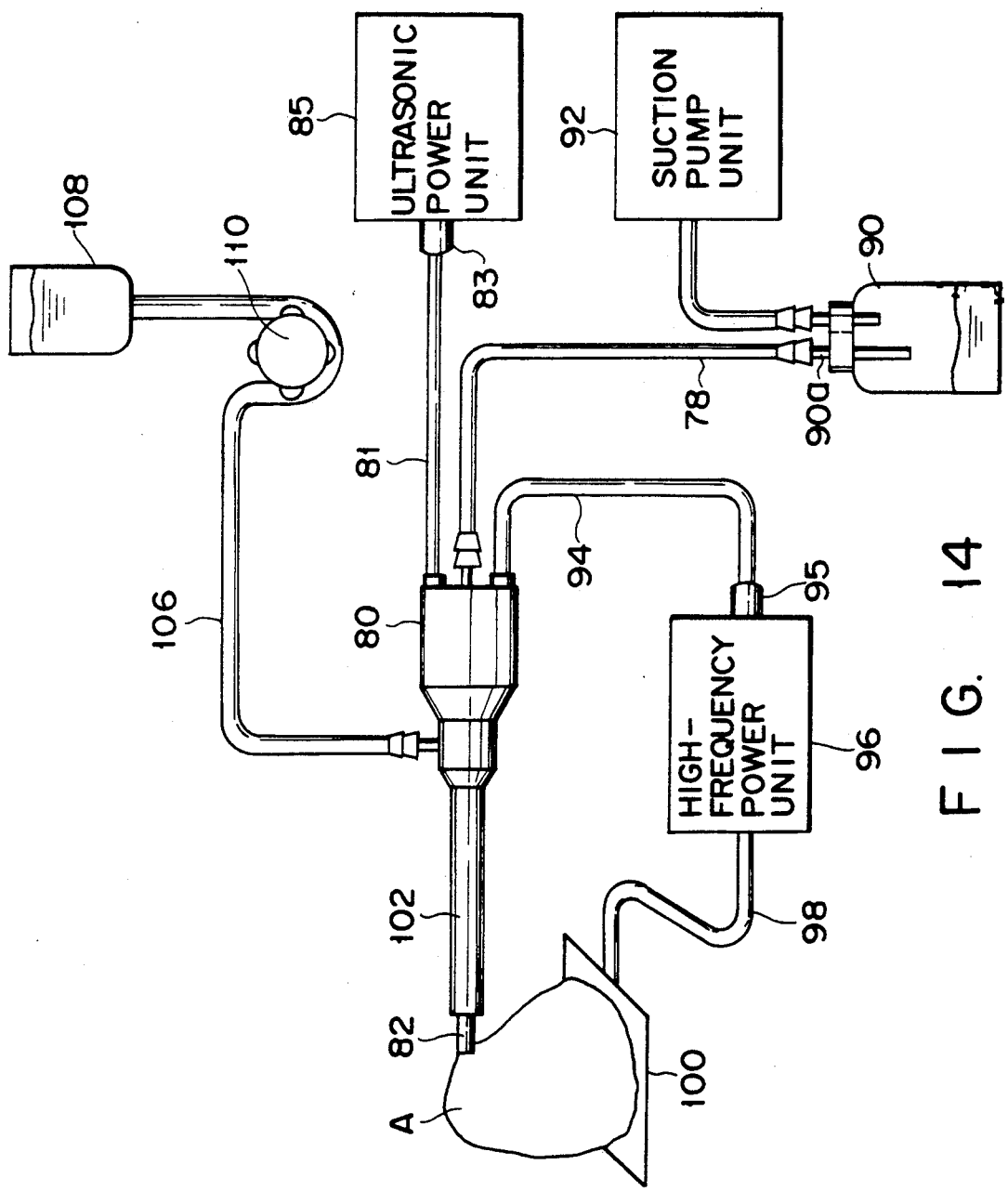
F I G. 14

MEDICAL INSTRUMENT

BACKGROUND OF THE INVENTION

1. Field of the Invention

The present invention relates to a medical instrument having an insertion section adapted to be inserted into a living body, such as an ultrasonic treatment apparatus, an endoscope, treatment means, or a resectosheath for guiding the endoscope or treatment means into the body cavity.

2. Description of the Related Art

Improved endoscope apparatuses are widely used in recent years. In these apparatuses, an elongated insertion section is inserted into a living body to be used for the observation of internal organs in the body cavity, and treatment means for various treatments can be inserted as required into treatment means channels.

In inserting the treatment means or one such endoscope apparatus into the body cavity, an elongated hollow guide tube is inserted in advance into the living body, and the treatment means or the endoscope apparatus is inserted into the body cavity, for the treatment and observation therein by utilizing the guide tube.

The endoscope apparatuses of this type include, for example, high-frequency endoscope apparatuses which are used to resect tissues in the prostate, uterus, ureter, renal pelvis, etc. An example of these apparatuses is disclosed in Published Unexamined Japanese Utility Model Application No. 60-149616. In a resectoscope apparatus described in this application, an electrode for resection, along with an insertion section, is inserted through the urethra into the urinary bladder, and a high-frequency current is supplied to the electrode, whereby the prostate can be resected.

In general, a resectoscope apparatus comprises a hollow sheath adapted to be inserted into the body cavity, an operating section with a slider removably attached to the rear end of the sheath, and an observation scope removably attached to the operating section from the rear end side thereof. In this arrangement, an electrode for resecting tissue in the body cavity can be projected or retreated from the distal end of the sheath by means of the slider. The distal end of this electrode, which is bifurcated to form a loop, is housed in a sheath insertion section, and the proximal end portion of the electrode is fixedly connected to an electric contact of the slider.

In this resectoscope apparatus, the slider is moved back and forth while supplying a high-frequency current to the electrode which is held against an affected part. Thereupon, the electrode moves back and forth, so that the affected part can be resected or coagulated.

Generally, a sheath of a resectoscope apparatus or the like is composed of an insertion section, in the form of an elongated hollow tubular member adapted to be inserted into the body cavity, and a body section having a connecting portion continuous with the proximal side of the insertion section. Since the insertion section of the sheath is expected to be inserted into the body cavity of a patient, its outside diameter must be minimized in order to reduce invasion on the body cavity side.

Meanwhile, a scope for the observation of the affected part must be inserted into the sheath insertion section, and its diameter should be as large as possible for better observation performance. A perfusate is fed into the body cavity through the inside of the sheath insertion section for use as a duct. In order to secure a clear view field, a satisfactory amount of perfusate must be supplied, so that the greatest possible passage for the perfusate should be formed.

Under these circumstances, it is necessary to maximize the inside diameter of the sheath insertion section and minimize the outside diameter thereof. Preferably, therefore, the wall thickness of the sheath insertion section to be inserted into the body cavity should be minimized. At the same time, the insertion section must have a mechanical strength high enough to stand a crushing force acting thereon and a bending force produced when it is inserted into the body cavity.

Since the distal end portion of the sheath insertion section is touched by the looped electrode for resecting or coagulating the affected part by means of the high-frequency current, it should be formed of a material which has a good insulating property against the high-frequency current and a heat resistance of 300° C. or more to stand heat produced when the affected part is resected or coagulated.

In consideration of these circumstances, the conventional sheath insertion section is formed of a metallic pipe, such as a stainless-steel pipe, which can enjoy a high mechanical strength despite its thin wall. A beak, which is formed of epoxy resin improved in heat resistance by being mixed with glass or ceramic fibers, is fitted in the distal end portion of the sheath insertion section, and fixed by adhesive bonding or the like, whereby the distal end portion is insulated from the looped portion of the electrode.

With use of this arrangement, the insulation between the looped portion of the electrode and the distal end portion of the sheath insertion section can be maintained for certain. As mentioned before, however, the outside diameter of the sheath must be minimized, so that an insulating coating of a good thickness cannot be applied to the sheath insertion section. Although the sheath insertion section can be fully insulated from a DC current, therefore, it may possibly be subjected to a small leakage of the high-frequency current (usually hundreds of kilohertzes). In such a case, the high-frequency current may leak into the body cavity of the patient, thereby causing a burn or electric shock to the patient's body.

Since the metallic sheath insertion section and the beak are separate components, moreover, the beak may possibly fall off in the body cavity as the insertion section is inserted into the cavity.

In order to eliminate these drawbacks, some sheaths have an insertion section which is formed of a thin-walled cylinder of glass fiber cloth impregnated with epoxy resin. With use of these sheaths, there is no possibility of the beak falling off or a current leaking from the sheath insertion section into the body cavity, indeed. Since the core of these sheaths is made of glass fiber cloth, however, its wall is inevitably thick. As compared with about 0.5 mm for the wall thickness of a metallic pipe, such as a stainless-steel pipe, a wall thickness of 0.7 mm or more is required of the glass-cloth sheaths. Thus, the outside diameter of the insertion section is inevitably large.

If he insertion section has a large outside diameter, invasion on the body cavity side is substantial. It is very troublesome and time-consuming, moreover, to prepare the glass fiber cloth, impregnate it with the epoxy resin, and form the resulting structure into a cylinder, so that the insertion section is expensive.

There are very few electrically insulating thermoplastic resins which have a heat resistance of 300° C. or more. They include, for example, polyether-etherketone (PEEK) and polyamide-imide (PAI). These heat-resistant thermoplastic resins are too poor in melt-flow characteristics to be used for the manufacture of a long thin-walled pipe (about 20 cm long and 0.5 mm thick) by injection molding or extrusion molding. It is difficult, therefore, to use these resins as materials for the sheath.

The above is a description of the sheath of the resectoscope apparatus which is adapted to be inserted into the urinary bladder per urethra for some treatments, such as the resection of the prostate. The aforementioned problems are not, however, peculiar to the sheath of the resectoscope, and lie also in the insertion sections of other medical instruments. These instruments include, for example, the sheath of a cystourethroscope apparatus and a thoracal mantle tube in which a guide tube called a thoracal is stuck into the abdominal wall, and a scope or treatment means is inserted into the thoracal to enable the observation of internal organs inside the abdominal wall or high-frequency treatment.

SUMMARY OF THE INVENTION

The object of the present invention is to provide a medical instrument adapted to be inserted into a living body, such as a resectoscope, ultrasonic treatment apparatus, endoscope, treatment means, thoracal mantle tube, etc., in which an insertion section to be inserted into the body cavity has an electrical insulating property and heat resistance, and its outside diameter is shortened without reducing its mechanical strength, so that invasion to a patient's body can be reduced.

The above object of the present invention is achieved by the following medical instrument. The medical instrument comprises: an operating section; and an insertion section connected to the operating section and adapted to be inserted into a living body, the insertion section including a tubular member formed of a liquid crystal polymer.

The tubular member constituting the insertion section of the medical instrument or a channel tube disposed in the insertion section is formed thin-walled by using the liquid crystal polymer. Thus, the electrical insulating property and heat resistance of the insertion section can be improved, and its outside diameter can be shortened.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 14 is a diagram showing the general configuration of the ultrasonic treatment apparatus;

DETAILED DESCRIPTION OF THE PREFERRED EMBODIMENTS

Preferred embodiments of the present invention will now be described in detail with reference to the accompanying drawings.

Figure 1:
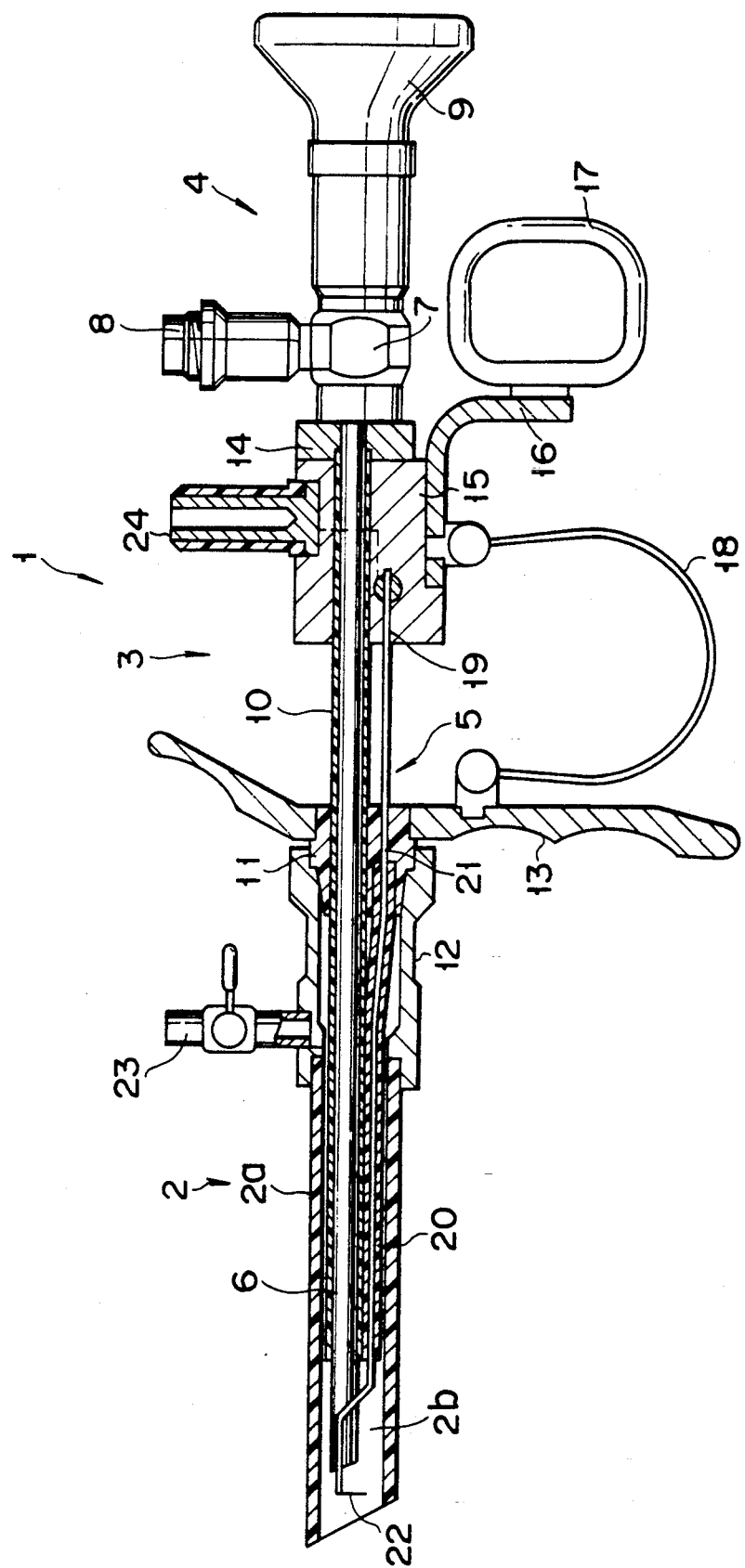
FIG. 1 is a cutaway side view of a resectoscope apparatus as a medical instrument according to a first embodiment of the present invention.
Figure 2:
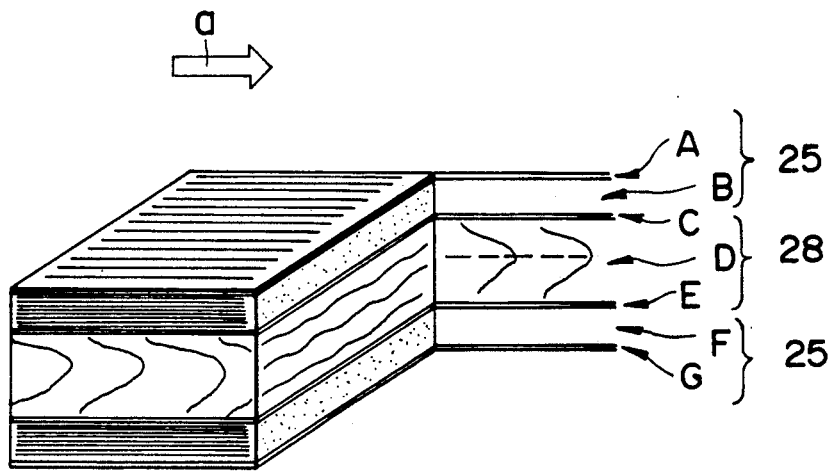
FIG. 2 is a partial view showing the sectional structure of an insertion section.
Figures 3, 4, 5:
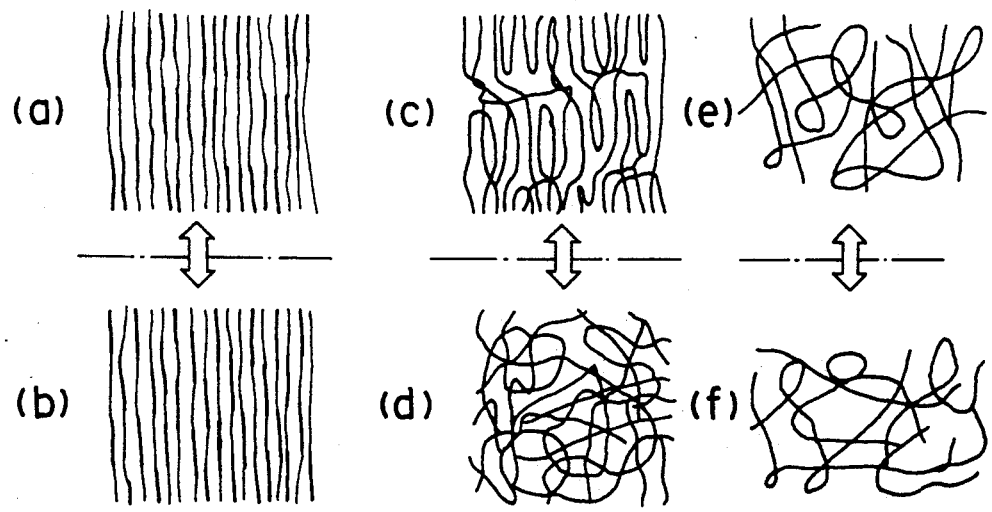
FIG. 3 is a diagram showing the molecular structure of a liquid crystal polymer.
FIGS. 4 and 5 are diagrams showing the molecular structures of conventional thermoplastic resins.

FIG. 1 shows a profile of a resectoscope apparatus as a medical instrument according to a first embodiment of the present invention. FIG. 2 shows a skin-core structure of a molded liquid crystal polymer article. FIGS. 3, 4 and 5 comparatively show molten and solid states of a liquid crystal polymer and other thermoplastic resins.

As shown in FIG. 1, the resectoscope apparatus 1 comprises a sheath 2 formed of a tubular member having an insertion section 2a adapted to be inserted into the body cavity, an operating section 3 removably attached to the rear portion of the sheath 2, an observation scope 4 adapted to be inserted into an insertion passage 2b of the sheath 2 from behind the section 3, and an electrode 5 adapted to be inserted into the passage 2b through the section 3.

The scope 4 is composed of a scope insertion section 6 adapted to be inserted into the sheath 2 through the operating section 3 and a proximal section 7. A light guide (not shown) and an optical system (not shown) for observation are fitted in the insertion section 6, and a light guide connector portion 8 for supplying illumination light to the light guide is attached to the flank of the proximal section 7. An eyepiece 9 is attached to the rear end portion of the proximal section 7. It is used to observe a subject image, which is illuminated by the illumination light guided through the light guide, and is transmitted by means of the optical system for observation.

The operating section 3 includes a guide tube 10 for retaining the scope 4, and a sheath connector portion 11 is fitted on the tube 10 near the central portion thereof. The connector portion 11 is removably coupled to a sheath body 12. Further, a finger hook 13 protrudes from the portion 11.

Meanwhile, a fixing portion 14 for fixing the scope 4 to a predetermined position is fixed to the rear end portion of the guide tube 10, and a slider 15 for electrode operation are loosely fitted for longitudinal sliding motion on that portion of the outer peripheral surface of the tube 10 which is situated between the fixing portion 14 and the sheath connector portion 11. A thumb ring 17 is fixed to the lower portion of the slider 15 by means of a downwardly bent plate member 16. A leaf spring 18 is disposed between the slider 15 and the finger hook 13 so that the slider 15 can be kept on stand-by, abutting against the fixing portion 14, by means of the urging force of the spring 18.

An electrode insertion tube 20 extends substantially parallel to the guide tube 10 under the same. The rear end portion of the tube 20 is fixed to the sheath connector portion 1 so as to communicate with an electrode insertion hole 21 bored through the connector portion 11.

The slider 15 is formed having an electrode insertion hole 19 which extends parallel to the longitudinal direction of the guide tube 10 from the front end face of the slider 15. An electrode cord connector portion 24, which is adapted to be connected to a high-frequency power source (not shown), is provided on the flank of the slider 15. In the slider 15, the connector portion 24 is connected electrically with the electrode 5. The electrode 5 is inserted into the electrode insertion hole 20 through the front end portion thereof, and its rear end is inserted through the sheath connector portion 11 into the insertion hole 19, and is fixed by using screw means (not shown) or the like.

An arcuate loop 22, whose inside diameter is a little smaller than that of the distal end portion of the insertion section 2a of the sheath 2, is formed on the front end portion of the electrode 5. The whole surface of the electrode 5 is covered for insulation except the loop 22 and its rear end portion which is to be inserted into the electrode insertion hole 19.

The sheath 2 has the insertion section 2a which is obtained by, for example, injection-molding a liquid crystal polymer in the form of a hollow elongated tube with a wall thickness of 0.5 mm or less and high heat resistance (load-deflection temperature of 300° C. or more). The cylindrical sheath body 12, which communicates with the insertion section 2a, is fixedly connected to the rear end of the section 2a by adhesive press fitting or the like. The body 12 has a water supply port 23 through which a liquid, such as a perfusate, is injected into the body 12.

The following is a description of the insertion section 2a formed of the liquid crystal polymer.

The injection-molded liquid crystal polymer article is composed of seven different layers shown in FIG. 2, by which it is discriminated distinctly from other molded resin articles. Roughly speaking, these layers include skin layers 25 composed of molecular chains arranged in the flowing direction indicated by arrow a in FIG. 2, near the surfaces of the injection-molded article, and a core layer 28 composed of a molecular chain arranged at right angles to the flowing direction indicated by arrow a, near the inner part of the molded article. The skin layers 25, whose molecular chains are oriented firmly and closely, are very conducive to the strength of the molded article. The smaller the wall thickness of the injection-molded article, the better the orientation of the molecular chains is, and the higher the percentage of the high-strength skin layers 25 is, that is, the less the core layer 28 is. Thus, the liquid crystal polymer, in contrast with the other resins, is characterized in that molded articles made of it increase their mechanical strength as their wall thickness is reduced.

In the molten state, as shown in FIG. 3(b), the liquid crystal polymer is in the form of a liquid crystal having molecules arranged in one direction without intertwining with one another, so that it can be caused to flow by a slight shearing stress. Thus, the liquid crystal polymer exhibits much better flow properties than conventional thermoplastic resins shown in FIGS. 4(d) and 5(f) whose molecules intertwine one another, so that it can be injection-molded into a thinwalled elongated pipe which cannot be formed from other heat-resisting resins. FIGS. 3(a), 4(c) and 5(e) show the solid state, while FIGS. 3(b), 4(d) and 5(f) show the molten state.

In the molded liquid crystal polymer article, moreover, the skin layers 25 enable the surfaces of the article to stand medical fluids, ethylene oxide gas, autoclave sterilization, etc. when the sheath 2 is subjected to disinfection.

It is to be understood, furthermore, that the liquid crystal polymer, like other synthetic resins, has a good electrical insulating property.

Liquid crystal polymers suited for use as the material of the insertion section 2a include thermotropic liquid crystal polymers having liquid crystal structures, such as nematic liquid crystal, cholesteric liquid crystal polymer, etc.

Commercially available liquid crystal polymers include XYDAR and Econol (terpolymer of hydroxybenzoic acid, biphenol, and terephthalic acid) from Dartco and Sumitomo Chemical, respectively, Vectora from Polyplastic, and Ueno (terpolymer of 2-oxy-6-naphthoic acid, biphenol, and terephthalic acid) from Ueno Seiyaku, etc.

Glass fibers having a length not long enough to prevent a resin flow during the injection molding and ceramic fibers, such as alumina fibers, silicon carbide fibers, etc., may be added as required to the liquid crystal polymer. The addition of these fibers can improve the mechanical strength and heat resistance of the insertion section, compared with the case in which the liquid crystal polymer is used singly.

Further, the molded article formed of the liquid crystal polymer can be made suitable for use in a hydrophilic lubrication process for forming a hydrophilic lubricant layer by graft-polymerizing hydrophilic molecular chains on the outer surface thereof. Thus, the outer surface of the insertion section formed of the liquid crystal polymer is subjected as required to the hydrophilic lubrication. By doing this, the outer surface of the insertion section can be wetted with water so that the hydrophilic lubricant layer captures water as the insertion section is inserted into the body cavity. As a result, the slip characteristic with a mucous membrane of the body wall is improved, so that the insertion section can be smoothly inserted into the body cavity.

Preferably, the hydrophilic high-molecular chains are polymers which are water-soluble and contain no radical ions at normal temperature or raised temperature. Such polymers include acrylamide polymers, methacrylamide polymers, polyvinyl pyrrolidone, polyvinyl alcohol, and polyethylene glycol dextran.

The following is a description of the operation of the resectoscope apparatus according to the first embodiment.

In starting the operation of the resectoscope apparatus 1 constructed in this manner, the electrode cord connector portion 24 is connected to the high-frequency power source (not shown) by means of a power cord (not shown). Then, the insertion section 2a of the sheath 2 is inserted into the urethra, part of the body cavity of a patient, and pushed into the urinary bladder.

Then, keeping the sheath 2 in the patient's body cavity, an operator anchors the thumb of one of his or her hands to the thumb ring 17, and pulls the finger hook 13 by means of the fingers of the same hand, thereby advancing the slider 15. Thereupon, the electrode 5 fixed to the slider 1 advances together with the slider 15, and the loop 22 on the front end portion of the electrode 5 projects from the front end portion of the sheath 2. While observing the affected part through the scope 4, the operator situates the affected part between the loop 22 and the front end portion of the sheath 2, and supplies electric power from the high-frequency power source to the loop 22.

Subsequently, when the press on the slider 15 is removed, the slider 15, along with the loop 22, is retreated by the urging force of the leaf spring 18, so that the affected part can be nipped between the front end portion of the sheath 2 and the loop 22. Since the loop 22 is supplied with a high-frequency current, it can be used to burn off the nipped affected part.

In burning off the nipped affected part, heat is produced and sometimes may be transmitted to the front end portion of the insertion section 2a. Since the insertion section 2a is formed by, for example, injection-molding the liquid crystal polymer having high heat resistance, it cannot be deformed by the heat.

Since the liquid crystal polymer has a high electrical insulating property, moreover, the high-frequency current cannot flow through the insertion section 2a into the patient's body cavity when it is supplied through the electrode 5 to the loop 22.

In the resectoscope apparatus according to the first embodiment, as described above, the insertion section 2a of the sheath 2 is formed thin-walled by injection-molding the liquid crystal polymer, so that the outside diameter of the insertion section 2a can be shortened without reducing its mechanical strength which should be high enough to stand a crushing or bending force. Thus, a current can be prevented from leaking from high-frequency treatment means such as the electrode 5, introduced into the sheath 2, into the body cavity through the insertion section 2a. Also, the insertion section 2a can be prevented from being distorted by heat produced by the high-frequency treatment, and invasion can be reduced when the sheath 2 is inserted into the body cavity, such as the urinary bladder or urethra.

Figure 6:
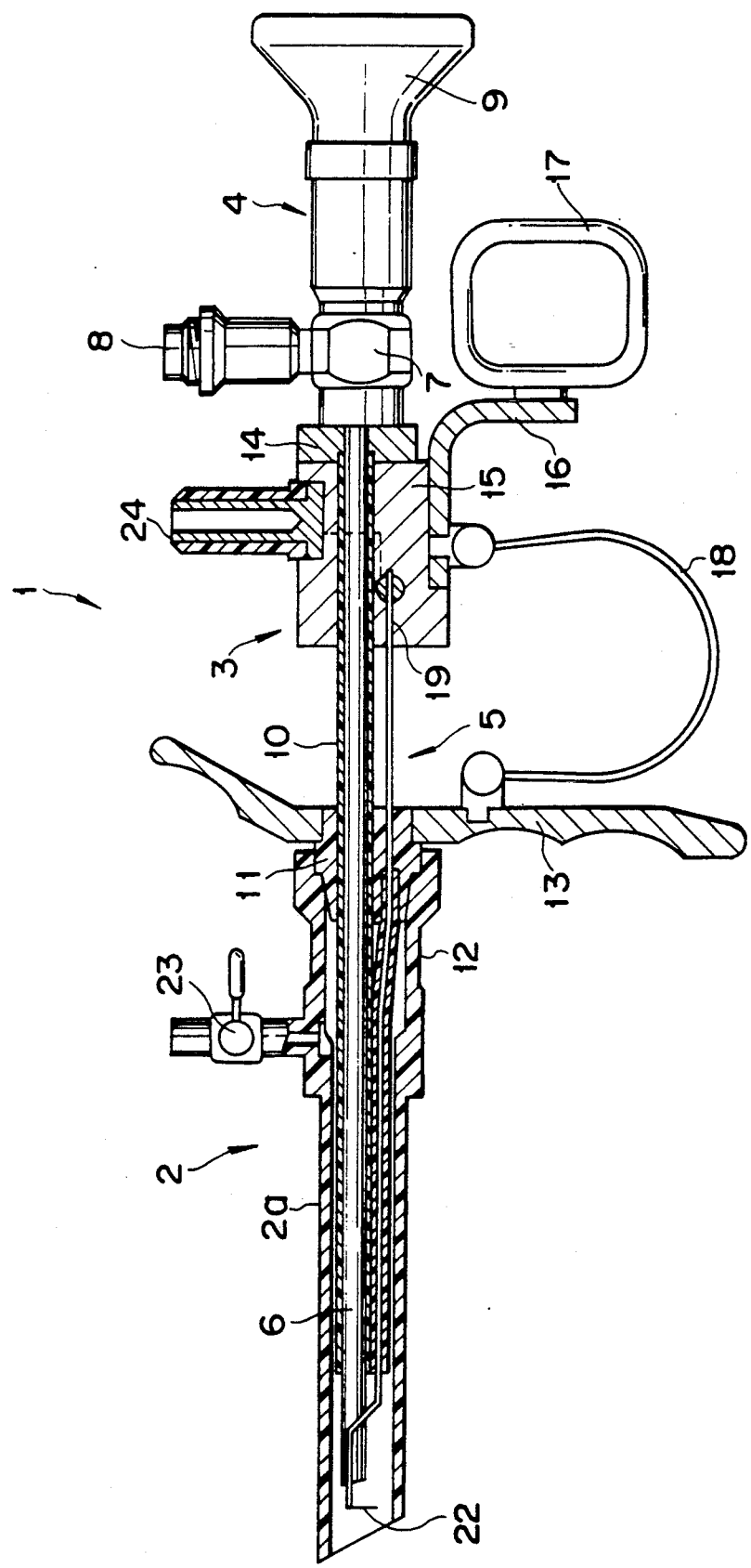
FIG. 6 is a cutaway side view of a resectoscope apparatus as a medical instrument according to a second embodiment of the invention.

FIG. 6 is a sectional view showing a resectoscope apparatus as a medical instrument according to a second embodiment of the present invention. In the description to follow, like members are designated by like reference numerals for simplicity.

In this second embodiment, an insertion section 2a of a sheath 2, in the form of a tubular member, a sheath body 12, and a water supply port 23 are formed of a liquid crystal polymer having high heat resistance, that is, they are integrally formed by utilizing the high fluidity of the liquid crystal polymer during the injection molding thereof.

The second embodiment can provide the following effects besides the same effects of the first embodiment. Since the insertion section 2a and the sheath body 12 of the sheath 2 are integrally formed, the section 2a cannot be disengaged from the body 12 during an operation.

Since the sheath body 12 and the insertion section 2a are integrally formed from the liquid crystal polymer, an insulating material, moreover, a high-frequency current can be prevented from leaking through the insertion section 2a into a patient's body cavity, and also from leaking through the sheath body 12 into the patient's body.

Since the number of components can be reduced, furthermore, the trouble of adhesive bonding or joining can be saved.

Figure 7:
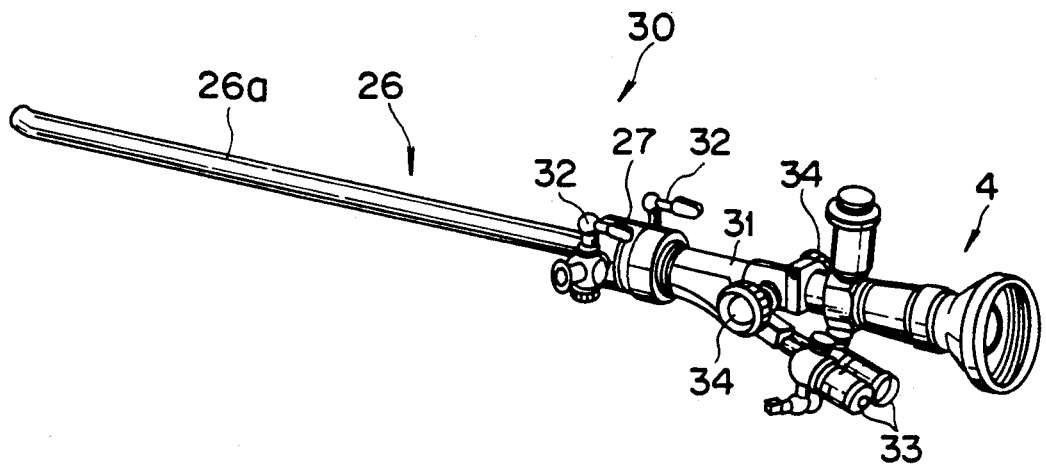
FIG. 7 is a perspective view of a cystourethroscope apparatus as a medical instrument according to a third embodiment of the invention.
Figure 8:
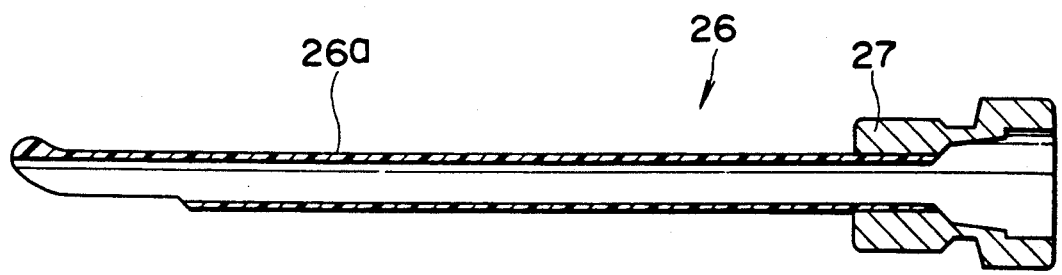
FIG. 8 is a longitudinal sectional view of a sheath of the cystourethroscope apparatus shown in FIG. 7.

FIGS. 7 and 8 show a cystourethroscope apparatus as a medical instrument according to a third embodiment of the present invention. FIG. 7 shows an outline of the cystourethroscope apparatus in which a sheath and a scope are connected by means of a bridge, and FIG. 8 shows a profile of the sheath.

The present embodiment relates to the cystourethroscope apparatus 30 in which the sheath 26 in the form of a tubular member is inserted through the urethra, and the scope 4 or treatment means (not shown) is inserted with the sheath 26 used as a guide, whereby the inside of the urinary bladder or urethra is observed and treated.

As shown in FIG. 7, the cystourethroscope apparatus 30 comprises the sheath 26, the bridge 31 removably mounted on the rear portion of the sheath 26, and the scope 4 for observation adapted to be inserted into the sheath 26 from the back of the bridge 31.

As shown in FIGS. 7 and 8, the sheath 26 is composed of an insertion section 26a formed by, for example, injection-molding a liquid crystal polymer into a thin-walled elongated pipe, and a sheath body 27 fixed to the rear end side of the section 26a by adhesive bonding, welding, or the like. A pair of taps 32 for gas and water supply are arranged on either side of the body 27. The bridge 31 is provided with a pair of forceps ports 33, through which treatment means such as a forceps (not shown) or high-frequency treatment means for cauterizing the affected part or arresting bleeding can be inserted into the insertion section 26a of the sheath 26 to be projected from the distal end thereof. Further, the bridge 31 is provided with a treatment means operating member 34. By operating this member 34, the treatment means projecting from the distal end of the insertion section 26a can be raised.

Meanwhile, the scope 4 is connected to the rear end portion of the bridge 31. The distal end of an insertion section of the scope 4 can be passed through the bridge 31 and the sheath 26 to be located on the distal end side of the insertion section 26a of the sheath 26, so that the inside of the body cavity or the like can be observed through an optical observation system of the scope 4.

The sheath 26 of the cystourethroscope apparatus 30 of the present embodiment, like the sheath 2 described in connection with the second embodiment, can be designed so that the insertion section 26a, the sheath body 27, and part of each tap 32 are integrally formed by utilizing the high fluidity of the liquid crystal polymer during the injection molding thereof.

The following is a description of the operation of the cystourethroscope apparatus according to the third embodiment.

In starting the operation of the cystourethroscope apparatus 30 constructed in this manner, the insertion section 26a of the sheath 26 is inserted into the urethra, part of the body cavity of a patient, and pushed into the urinary bladder. After the sheath 26 is inserted in this manner, the bridge 31 is connected to the rear end portion of the sheath body 27. Then, the scope 4 is connected to the rear end portion of the bridge 31 so that the distal end of the insertion section of the scope 4 is passed through the bridge 31 and the sheath 26 to be situated at the distal end of the insertion section 26a. In this state, the inside of the urinary bladder or urethra is observed.

The treatment means such as the forceps (not shown) or the high-frequency treatment means for cauterizing the affected part or arresting bleeding is inserted through the forceps ports 33 of the bridge 31, and is passed through the insertion section 26a of the sheath 26 to be projected from the distal end thereof. Further, an operating member 34 attached to the bridge 31 is operated as required to raise and bring the treatment means close to the affected part so that biopsy, cauterization by means of a high-frequency current, or stanching can be effected.

Figure 9:
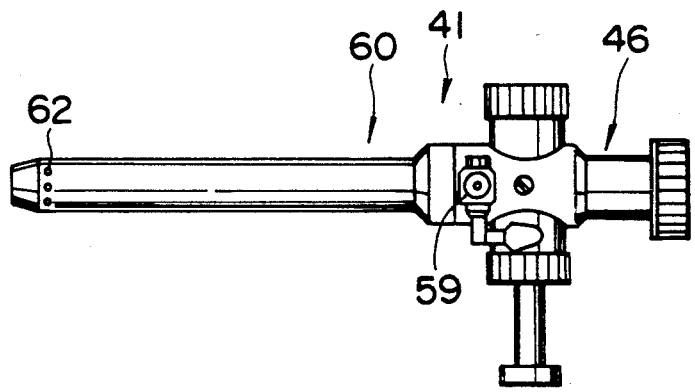
FIG. 9 is a side view of a thoracal mantle tube as a medical instrument according to a fourth embodiment of the invention.
Figure 10:
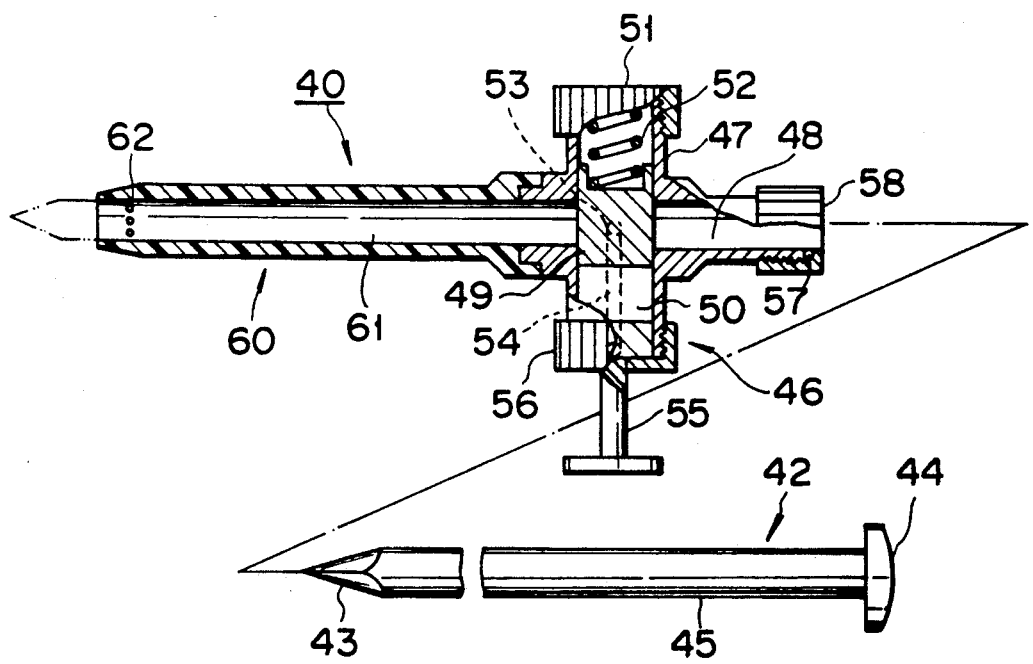
FIG. 10 shows a profile of the thoracal mantle tube and a side view of a thoracal needle.

FIGS. 9 and 10 show a thoracal as a medical instrument according to a fourth embodiment of the present invention. FIG. 9 shows a thoracal mantle tube, which is adapted to be stuck and retained in the body wall, such as the abdominal wall, to serve as a guide for treatment means, e.g., an endoscope, a forceps such as a biopsy forceps for extracting tissue pieces, or high-frequency treatment means for cauterizing the affected part or arresting bleeding by means of a high-frequency current, which is to be inserted into the body cavity. FIG. 10 shows a profile of the thoracal mantle tube and a side view of a thoracal needle.

In the thoracal 40 of the present embodiment, the thoracal needle 42 is composed of a distal end portion, shaped like a trigonal pyramid, and a columnar insertion rod 45 having a grip 44 on the proximal side.

The thoracal mantle tube 41 comprises an insertion section 60, in the form of a tubular member, and a body 46 having a cylinder 47 extending at right angles to the axis of the section 60. A piston 49 is slidably disposed in the cylinder 47. It serves to close a duct 48, which extends in the axial direction of the insertion section 60, thereby preventing a leakage of air. The piston 49 has a communication hole 50 communicating with the duct 48. It is normally urged to close the duct 48 lest the duct 48 and the hole 50 communicate with each other, by means of the urging force of a spring 52 interposed between the piston 49 and a cap 51, which is used hermetically to seal one opening of the cylinder 47.

A pin 53 protrudes outward from the piston 49. It is fitted in a guide groove 54 formed inside the cylinder 47 so as to extend in the axial direction thereof, thereby restraining the piston 49 from rotating. A pressure rod 55 is located on the opposite side of the piston 49 to the spring 52. It extends to the outside through a piston cap 56 which is used hermetically to seal the other opening of the cylinder 47.

A packing gland 58 having a packing 57 therein is mounted on the rear end portion of the thoracal mantle tube 41 so that the outer peripheral surface of the thoracal needle 42 is intimately in contact with the packing 57, whereby air can be prevented from leaking through the duct 48. A tap 59 for pneumoperitoneum gas protrudes from the flank of the cylinder 47 so as to communicate with the duct 48.

The insertion section 60, which extends forward from the body 46, is fixedly connected to the distal end portion of the body 46 by screwing or the like. The section 60 is formed by injection-molding a liquid crystal polymer. The thoracal needle 42, endoscope, and some other treatment means can be inserted into the insertion section 60, which is formed having a duct 61 communicating with the duct 48 of the body 46 and the communication hole 50. The inside diameter of the duct 61 is substantially equal to or a little greater than the outside diameter of the thoracal needle 42. A plurality of vent holes 62 are formed in the near end portion of the peripheral wall of the insertion section 60 so as to communicate with the duct 61.

The following is a description of the operation of the thoracal according to the fourth embodiment.

First, the thoracal needle 42 is inserted into the duct 48 from the proximal side of the body 46 of the thoracal mantle tube 41, as indicated by dashed line in FIG. 10. Then, the pressure rod 55 is pushed to allow the communication hole 50 to communicate with the duct 48 of the body 46 and the duct 61 of the insertion section 60. While doing this, the thoracal needle 42 and the thoracal mantle tube 41 are combined together as indicated by broken line in FIG. 10. Thereafter, the combination of the needle 42 and the tube 41 are stuck into the body wall such as the abdominal wall. Since the insertion section 60 of the thoracal mantle tube 41 is a thin-walled elongated pipe formed by injection-molding the liquid crystal polymer, its outside diameter can be shortened without reducing its mechanical strength, as in the cases of the foregoing embodiments. Thus, the needling can be performed with ease.

Subsequently, after the combination of the thoracal needle 42 and the thoracal mantle tube 41 is stuck into the body wall, the needle 42 is drawn out from the tube 41, and a scope (not shown) is inserted instead for the observation of the inside of the body cavity. Further, the forceps such as the biopsy forceps for extracting tissue pieces or the high-frequency treatment means for cauterizing the affected part or arresting bleeding by means of a high-frequency current is inserted into the body cavity to effect various treatments. Since the insertion section 60 is formed of insulating material, the high-frequency current for the treatment can never leak through the section 60 into the patient's body cavity.

Figure 11:
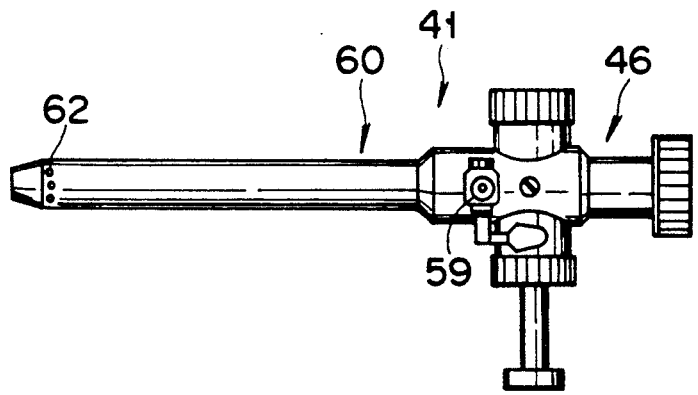
FIG. 11 is a side view of a thoracal mantle tube as a medical instrument according to a fifth embodiment of the invention.
Figure 12:
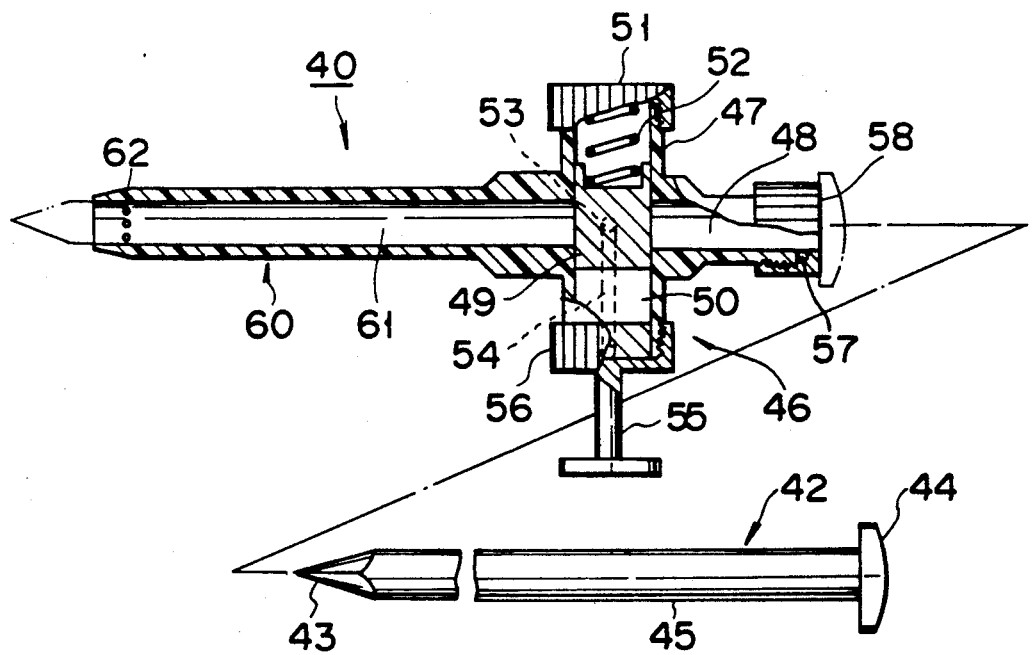
FIG. 12 shows a profile of the thoracal mantle tube of FIG. 11 and a side view of a thoracal needle used therewith.

FIGS. 11 and 12 show a fifth embodiment of the present invention. In the description to follow, like members are designated by like reference numerals for simplicity.

A thoracal 40 of the present embodiment is constructed in the same manner as that of the fourth embodiment, provided that an insertion section 60 and a body 46 are integrally formed by, for example, injection-molding a liquid crystal polymer. Also in this arrangement, the outside diameter of the insertion section 60 of the thoracal 40 can be shortened, and the electrical safety can be improved.

Figure 13:
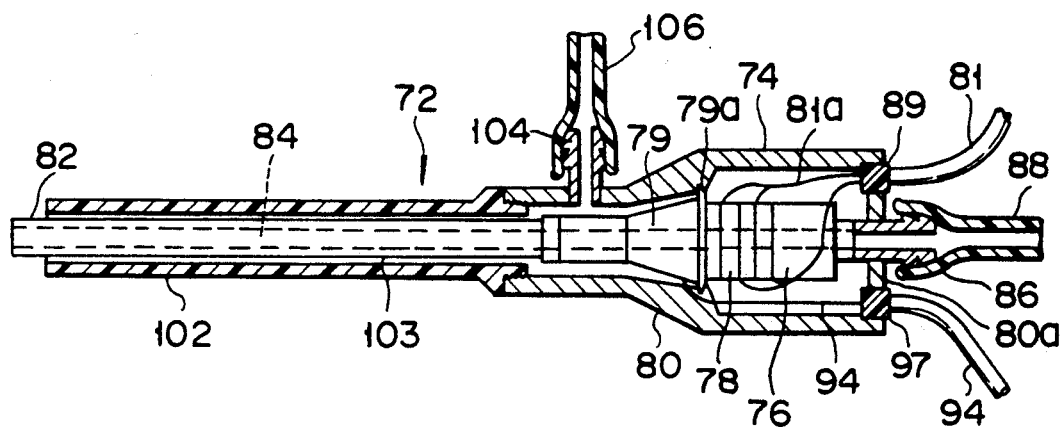
FIG. 13 is a longitudinal sectional view of an ultrasonic treatment apparatus as a medical instrument according to a sixth embodiment of the invention.

FIGS. 13 and 14 show an ultrasonic treatment apparatus as a medical instrument according to a sixth embodiment of the present invention.

As shown in FIG. 13, the ultrasonic treatment apparatus of the present embodiment comprises a hand piece 72 used to cure affected tissue in a living body. A grip portion 74 of the hand piece 72 is provided with a Langevin ultrasonic vibrator 76, which includes a horn 79 for amplifying the amplitude of ultrasonic vibration and a vibration generator unit 78 having piezoelectric elements and electrodes arranged in alternate layers. The generator unit 78 is clamped to the horn 79 by means of bolts and nuts (not shown). A flange 79a, which protrudes from the outer periphery of the rear end portion of the horn 79, is fixed to a vibrator cover 80 which covers the ultrasonic vibrator 76. A lead wire 81a of an ultrasonic power cord 81 is connected to the electrodes of the vibration generator unit 78, and the proximal end of the cord 81 is connected to an ultrasonic power unit 85 by means of a power connector 83. The distal end of the power cord 81 is fixed to a rear end wall 80a of the vibrator cover 80 by means of a power cord mouthpiece 89.

A vibration transmission member 82 formed of a hollow metallic pipe is fixed to the distal end of the horn 79. The horn 79 and the vibration generator unit 78 are formed having a through hole, which constitutes a suction passage 84 in conjunction with a hollow of the transmission member 82 communicating therewith. The passage 84 communicates with a suction mouthpiece 86 which penetrates the rear end wall 80a of the vibrator cover 80, and a suction bottle 90 is connected to the mouthpiece 86 by means of a suction tube 88 and a suction bottle mouthpiece 90a. Further, a suction pump unit 92 is connected to the bottle 90.

A lead wire 94a of a high-frequency power cord 94 is connected to the horn 79 so that a high-frequency power unit 96 is connected to the horn 79 by means of the cord 94 and a connector 95. Thus, a high-frequency current can be supplied to the vibration transmission member 82 which is fixed to the horn 79. Further, a P-plate 100, for use as a living-body-side electrode, is connected to the power unit 96 by means of a P-cord 98. In use, the plate 100 is brought into contact with living body tissue A. The proximal portion of the high-frequency power cord 94 is fixed to the rear end wall 80a of the vibrator cover 80.

A sheath 102 in the form of a tubular member is attached to the front portion of the vibrator cover 80 so as to cover the vibration transmission member 82. A water supply mouthpiece 104, which communicates with a water supply line 103 between the sheath 102 and the transmission member 82, is attached to the rear end portion of the sheath 102. A water supply tank 108 is connected to the mouthpiece 104 by means of a water supply tube 106. A water supply pump 110 formed of a roller pump is mounted in the middle of the tube 106. The pump 110 can supply the water supply line 103 with a perfusate, such as a physiological saline solution, and discharge the perfusate from the distal end of the sheath 102. The water supply mouthpiece 104 may alternatively be provided on the side of the sheath 102.

In this sixth embodiment, the sheath 102 is formed by, for example, injection-molding a liquid crystal polymer with high heat resistance. Besides, all the hand piece shell members except part of the vibration transmission member 82 projecting from the distal end of the sheath 102, including the vibrator cover 80, water supply mouthpiece 104, suction mouthpiece 86, ultrasonic power cord mouthpiece 89, high-frequency power cord mouthpiece 97, etc., are formed of insulating material.

In the ultrasonic treatment apparatus constructed in this manner, ultrasonic vibration generated by means of the vibration generator unit 78 is amplified by the horn 79, and transmitted through the vibration transmission member 82. As the distal end of the transmission member 82 undergoes ultrasonic vibration, the affected tissue A in contact therewith is resected. At the same time, the perfusate can be supplied from the water supply tank 108 through the water supply line 103 between the sheath 102 and the vibration transmission member 82, and sucked in through the suction passage 84 by means of the suction pump unit 92.

If the living body tissue bleeds during such resection, the high-frequency current is supplied through the horn 79 to the vibration transmission member 82. Thereupon, the high-frequency current flows through the bleeding tissue, so that the bleeding can be arrested by the blood coagulating effect of the current.

If the high-frequency current for stanching leaks during the treatment, it may possibly flow through the ultrasonic treatment apparatus itself, thereby giving an electric shock to the patient or operator. In the present embodiment, therefore, the all the hand piece shell members are formed of insulating material, so that the treatment can be safely given without entailing an electric leakage to the body of the patient or operator even though the high-frequency current for stanching is supplied to the vibration transmission member 82.

Since the sheath 102 is formed by injection-molding the liquid crystal polymer with high heat resistance into a thin-walled elongated pipe, moreover, the outside diameter of the insertion section can be shortened without reducing its mechanical strength, as in the cases of the foregoing embodiments, so that the sheath 102 can be easily stuck into the body cavity. The distal end of the sheath can be prevented from scorched or melted by heat produced when the high-frequency current is caused to flow through the vibration transmission member 82. Moreover, the distal end of the sheath can be prevented from being damaged by heat which is produced by the vibration of the transmission member 82 even though no high-frequency current is supplied to the member 82.

Figure 15:
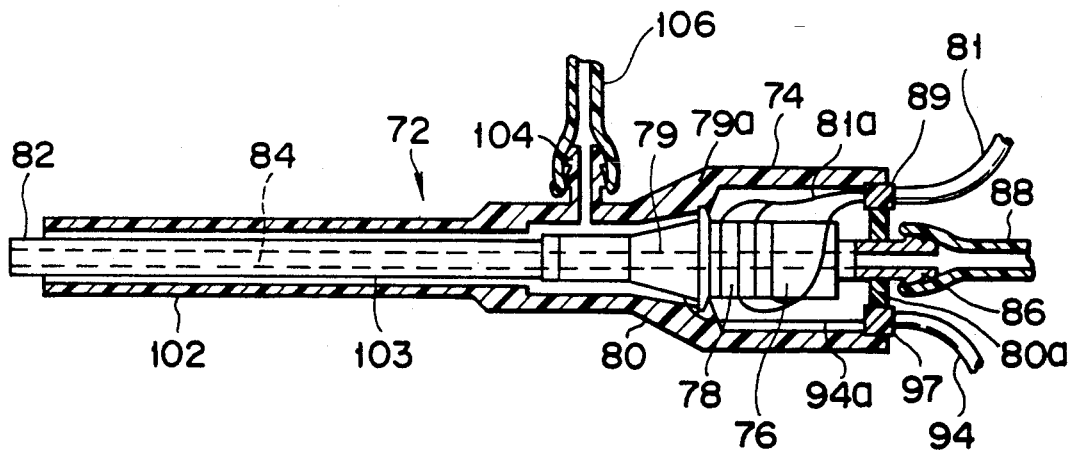
FIG. 15 is a longitudinal sectional view showing a modification of the ultrasonic treatment apparatus.

FIG. 15 shows a modification of the ultrasonic treatment apparatus according to the sixth embodiment. In the description to follow, like members are designated by like reference numerals for simplicity.

In this modification, the sheath 102, vibrator cover 80, and water supply mouthpiece 104 are integrally formed by utilizing the high fluidity of the liquid crystal polymer during the injection molding thereof.

Besides the effects of the sixth embodiment, therefore, this modification can therefore provide the following effects. Since the sheath 102 and the vibrator cover 80 are integrally formed, the sheath 102 cannot be disengaged from the cover 80 during an operation. Since the number of components can be reduced, moreover, the trouble of adhesive bonding or joining can be saved.

Figure 16:
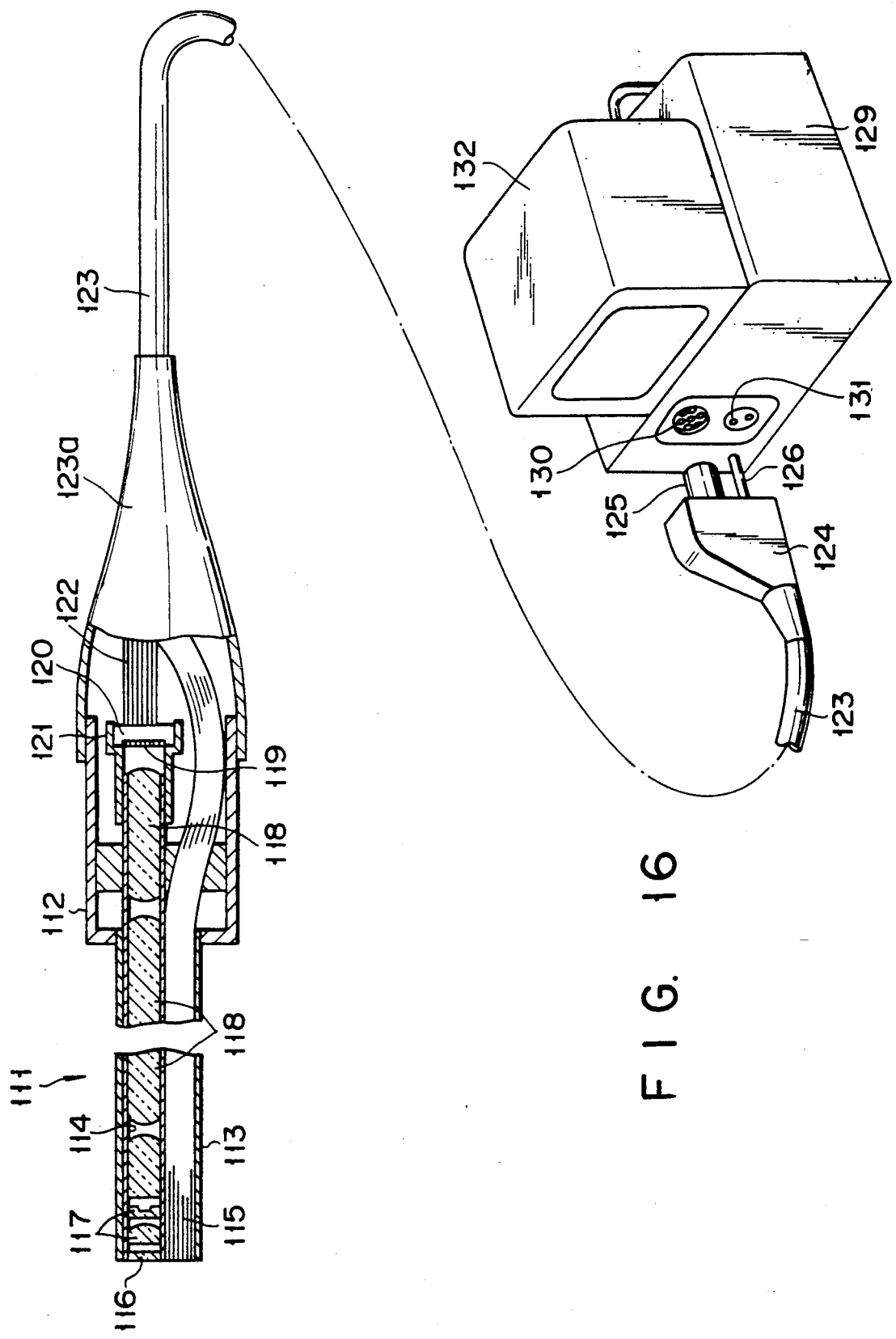
FIG. 16 is a cutaway side view showing an electronic endoscope apparatus as a medical instrument according to a seventh embodiment of the invention and a control device therefor.
Figure 17:
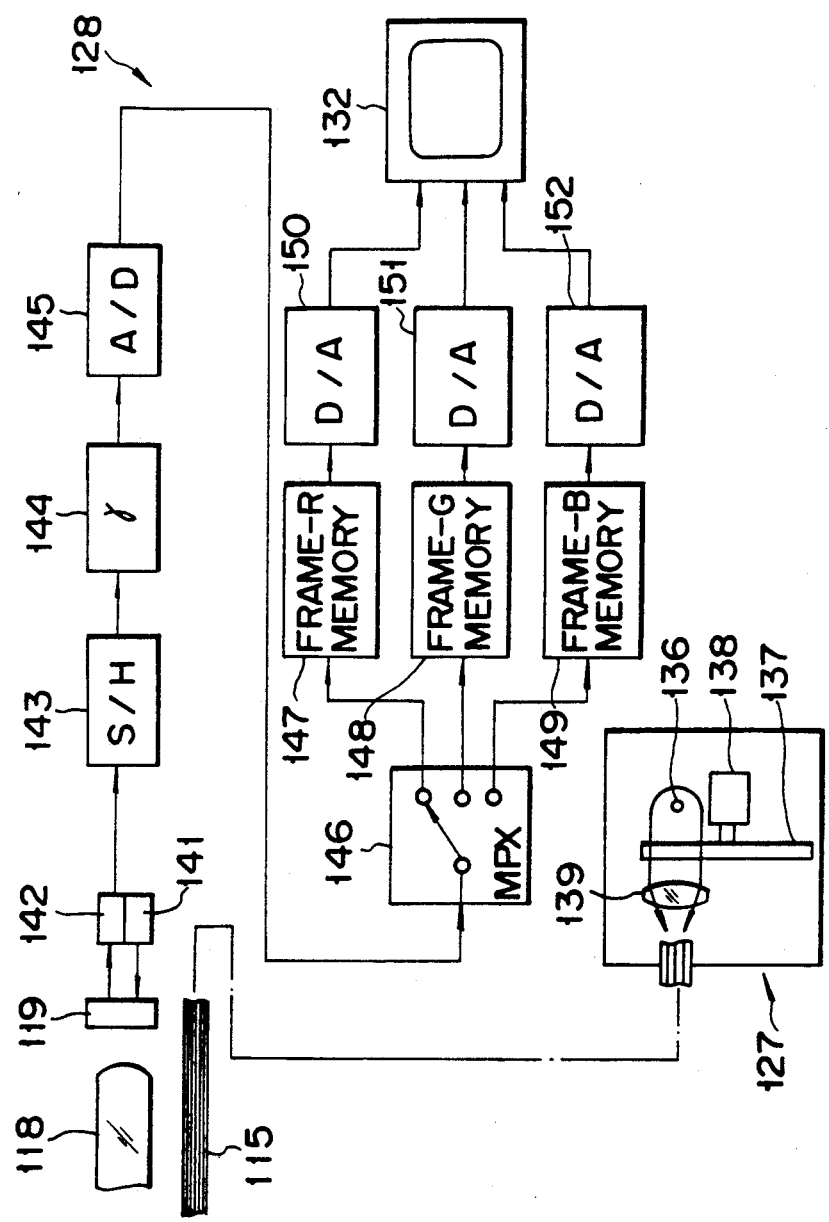
FIG. 17 is a block diagram showing an image processing circuit of the electronic endoscope.

FIGS. 16 and 17 show a rigid electronic endoscope as a medical instrument according to a seventh embodiment of the present invention. This endoscope may be used in place of, for example, the scope 4 shown in FIG. 1.

In FIG. 16, numeral 111 denotes the rigid electronic endoscope, which comprises an operating section 112, which doubles as a proximal grip portion, and a straight elongated insertion section 113 extending forward from the section 112. The body of the insertion section 113 is formed by injection-molding a rigid liquid crystal polymer with high heat resistance. A lens tube 114 and a light guide 115 formed of an optical fiber bundle are arranged in both the operating section 112 and the insertion section 113, extending substantially parallel to each other in the axial direction of the endoscope. The distal end of the guide 115 forms a light emitting end on the distal end face of the insertion section 113.

The lens tube 114, which extends to the distal end face of the insertion section 113, has a cover glass 116 in the distal end portion thereof. Objective lenses 117 are arranged in that portion of the tube 114 located behind the glass 116. A plurality of relay lenses 118 are arranged in that portion of the lens tube 114 which extends from behind the lenses 117 into the operating section 112. A solid-state image sensing device 119 is disposed in a focusing position behind the rearmost relay lens 118. The device 119 is fixed to a substrate 120 so as to be connected thereto by means of a bonding wire (not shown), the substrate 120 being attached to the rear end of the lens tube 114 by means of a frame 121. A large number of signal lines 122 are connected to the substrate 120.

A flexible cable 123 is integrally connected to the rear end of the operating section 112 by means of a connector portion 123a, and the light guide 115 and the signal lines 122 extend in the cable 123. A connector 124, which is provided with a power supply plug 125 and an illumination plug 126, is attached to an end portion of the cable 123.

A control device 129 of the electronic endoscope 111 contains therein a light source unit 127 and a video signal processing circuit 128, and comprises a power supply connector socket 130 and an illumination connector socket 131 to which the pugs 125 and 126 of the connector 124 are connected, respectively. A color CRT 132 constituting display means is connected to the control device 129.

As shown in FIG. 17, the light source unit 127 in the control device 129 includes a source lamp 136 and a rotating color filter 137 formed of three primary-color filters, red, green, and blue. The filter 137 is rotated by means of, for example, a stepping motor 138. A light emitted from the lamp 136 is converted into red, green, and blue light beams by means of the color filter 137, condensed by means of a condensing lens 139, and radiated from the distal end of the insertion section 113 through the light guide 115 in the cable 123, thereby illuminating an observed region according to the sequence of arrangement of the colors.

Red, green, and blue reflected light beams from the observed region are transmitted through the objective lenses 117 and the relay lenses 118, and received by an image area of an image sensing chip embedded in the solid-state image sensing device 119. In the case of a surface-sequential system, an output signal from the image area of the chip is subjected to video signal processing in the order shown in FIG. 17, for example.

Thus, signals corresponding to individual pixels of the solid-state image sensing device 119 are successively outputted, for example, in the transverse direction in response to clock signals delivered from a driver circuit 141. Electrical signals containing this image information are amplified by means of a preamplifier 142, and video signals are sampled therefrom in a sample-and-hold circuit 143, and $\gamma$-corrected in a $\gamma$-correction circuit 144. Thereafter, the corrected signals are converted into digital signals by means of an A/D converter 145. These electrical signals are switched in synchronism with the color-surface-sequential illumination by means of a multiplexer 146, and are stored in a frame-R memory 147, frame-G memory 148, and frame-B memory 149 which correspond to red, green, and blue, respectively. The signals in the frame memories 147, 148 and 149 are simultaneously transversely read out at a speed matched to the display device, such as the color CRT monitor 132, and are converted into analog signals by means of a D/A converters 150, 151 and 152, thus forming R, G, and B color signals, respectively. When these R, G, and B color signals are applied to the input of the CRT monitor 132, the observed region is displayed in colors.

Now let it be supposed that the rigid electronic endoscope 111 of the present embodiment is used as the scope shown in FIG. 1 for example. Since the body of the insertion section 113 of the endoscope 111 is formed by injection-molding the liquid crystal polymer with high heat resistance into a thin-walled elongated pipe, its outside diameter can be shortened without reducing its mechanical strength. Also, the in- and outside diameters of the guide tube 10 of the operating section 3 of the resectoscope apparatus, which is used to guide the insertion section 113 of the endoscope 111, can be shortened. Thus, the in- and outside diameters of the insertion section 113 of the endoscope 111 or the insertion section 2a of the sheath 2, which is used to guide the guide tube 10 of the operating section 3, can be also shortened, so that invasion can be reduced when the insertion section is inserted into the body cavity, such as the urinary bladder or urethra.

Since the insertion section 113 of the rigid electronic endoscope 111 is formed by injection-molding the liquid crystal polymer with high heat resistance, moreover, it cannot be distorted by heat which may be produced and transmitted to its distal end portion when the high-frequency current is supplied to the loop 22 to burn off the effected part. Since the liquid crystal polymer has a high electrical insulating property, furthermore, there is no possibility of the high-frequency current flowing through the insertion section 113 of the endoscope 111 to the solid-state image sensing element 119, thereby damaging the device 119 or adversely affecting the image, or of the current flowing through the operating section 112 to the operator.

In the present embodiment, the body of the insertion section of the rigid electronic endoscope is formed by injection-molding the liquid crystal polymer. However, the insertion sections of general rigid scopes may be also formed by injection-molding a liquid crystal polymer with the same effects.

As in the case of the embodiment shown in FIG. 15, moreover, the insertion section 113 and the operating section 112 of the rigid electronic endoscope 111 of the present embodiment can be integrally formed by injection-molding the liquid crystal polymer. By this integral forming, the high-frequency current can be more efficiently prevented from exerting a bad influence on the solid-state image sensing device 119, and from leaking to the operator's body.

Figure 18:
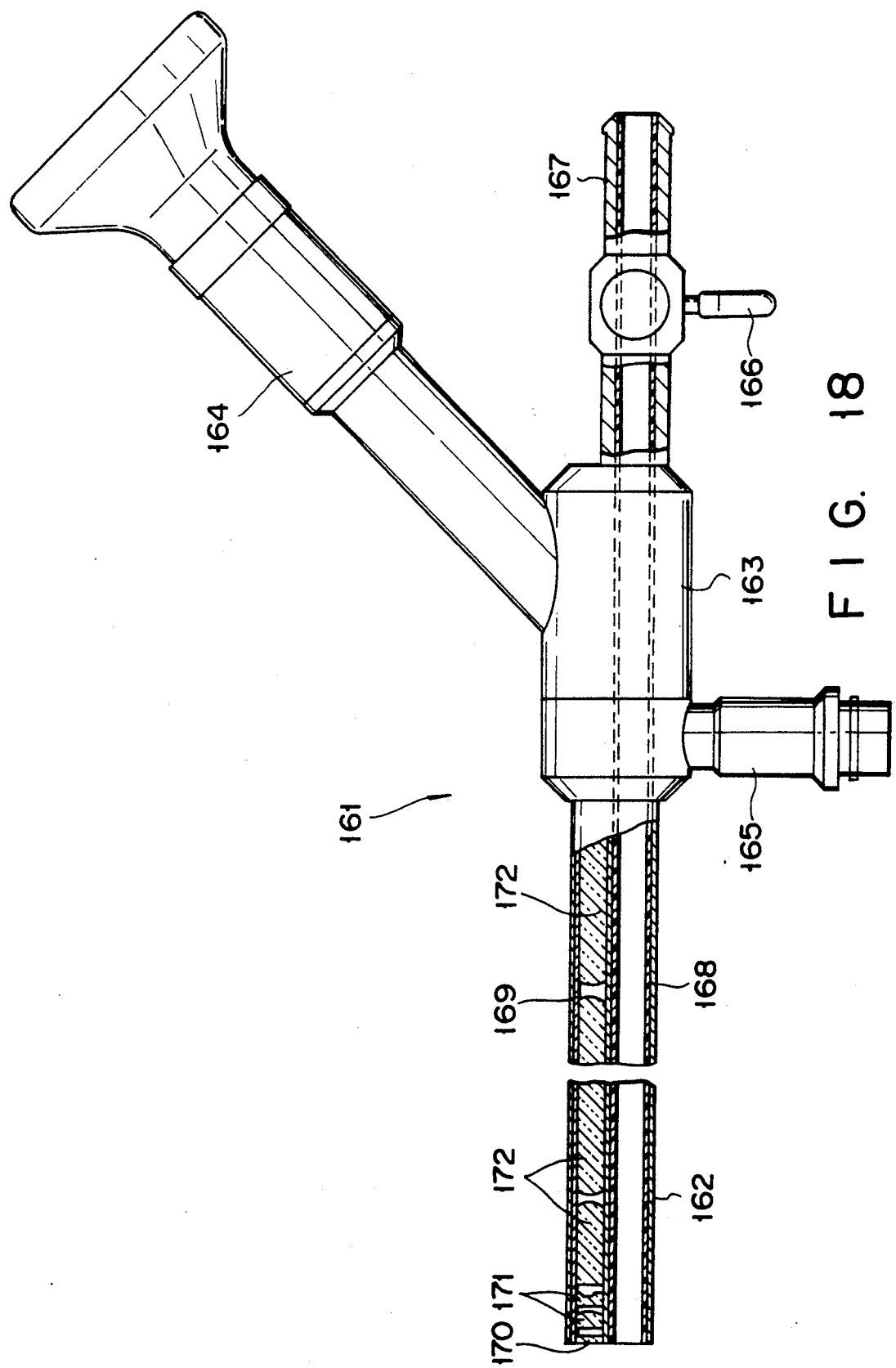
FIG. 18 is a cutaway side view of a scope with a forceps channel as a medical instrument according to an eighth embodiment of the invention.

FIG. 18 shows a scope 161 with a forceps channel as a medical instrument according to an eighth embodiment of the present invention.

The scope 161 comprises a straight elongated rigid insertion section 162, a body section 163 extending on the proximal side of the insertion section 162, and an eyepiece section 164 diagonally extending from the flank of the body section 163 toward the proximal side. A light guide mouthpiece 165 for the connection of a light guide cable (not shown) is attached to the bottom side of the body section 163. The light guide cable is used to supply illumination light emitted from a light source unit (not shown). A forceps port 167 having a gate tap 166 is attached to the proximal side of the body section 163.

A forceps channel 168 and a lens tube 169 in the form of an elongated pipe are arranged in the insertion section 162, body section 163, and forceps port 167, extending substantially parallel to each other. The channel 168, which is formed by injection-molding a liquid crystal polymer with high heat resistance into a thin-walled elongated pipe, is adapted to receive high-frequency treatment means or a biopsy forceps (not shown). A cover glass 170 is disposed in the distal end portion of the lens tube 169, and objective lenses 171 are arranged behind the glass 170. A plurality of relay lenses 172 are arranged in that portion of the lens tube 169 which extends from behind the lenses 171 into the body section 163 and the eyepiece section 164.

An eyepiece lens (not shown) is disposed in the vicinity of the proximal end face of the eyepiece section 164. An image of an object situated near the distal end of the insertion section 162 can be observed through the eyepiece section 164 by enlarging the object image, transmitted through the cover glass 170, objective lenses 171, and relay lenses 172, by means of the eyepiece lens.

The following is a description of the operation of the scope with a forceps channel according to the eighth embodiment.

The scope 161 of the present embodiment is inserted into the body cavity with use of, for example, the thoracal mantle tube 41 shown in FIG. 9 as a guide. Then, the distal end portion of the insertion section 162 is brought close to the affected part so that the affected part can be observed through the proximal end face of the eyepiece section 164. Depending on the state of the affected part, the gate tap 166 is switched to open the forceps channel 168, and the forceps or high-frequency treatment means (not shown) is introduced through the proximal end face of the forceps port 167 into the body cavity with use of the channel 168 as a guide. Thus, while observing the affected part, the operator can examine or resect it by means of the forceps, cauterize the affected part or arrest its bleeding by using the high-frequency treatment means, or resect or suck in the affected part with use of ultrasonic treatment means.

The forceps channel 168 of the scope 161 for guiding the treatment means into the body cavity is formed having an extremely thin wall by injection-molding the liquid crystal polymer with high heat resistance, so that its outside diameter can be shortened. As the outside diameter of the channel 168 is reduced in this manner, that of the insertion section 162 can be shortened correspondingly. Accordingly, the in- and outside diameters of the insertion section of the thoracal mantle tube 41 for guiding the scope 161 may be shortened, so that a needle hole in the patient's body wall can be made smaller. Thus, invasion to the patient's body can be reduced.

Since the forceps channel 168 is formed by injection-molding the liquid crystal polymer with high heat resistance, moreover, it cannot be distorted by heat which is produced during the cauterization of the affected part using the high-frequency treatment means or the like, and the current can be prevented from leaking to the patient's body cavity or the operator's body, due to the insulating property of the liquid crystal polymer.

Since the liquid crystal polymer forming the forceps channel 168 is high in both mechanical strength and heat resistance, as mentioned before, it cannot be distorted or damaged even when it is subjected to ultrasonic vibration attributable to the insertion of the ultrasonic treatment means therein.

For another effect, the inside diameter of the forceps channel 168 can be made greater than that of a conventional one, since its wall thickness can be reduced without shortening its outside diameter by injection-molding the liquid crystal polymer. In this case, the forceps channel 168 can guide treatment means with a greater outside diameter than the conventional one can, so that a scissors-type forceps with a greater outside diameter can be used. Accordingly, the affected part can be efficiently resected by means of a scissors-type forceps with a relatively large scissors section. Thus, the time required for the resection can be shortened, so that the operation time can be shortened. This effect can be also obtained with use of other biopsy forceps and other treatment means.

Also in the present embodiment, the forceps channel 168 and the forceps port 167, for example, can be integrally formed by utilizing the high fluidity of the liquid crystal polymer. By doing this, the high-frequency current can be more securely prevented from leaking through the port 167 to the operator's body.

Further, if the lens tube 169, insertion section 162, and body section 163, as well as the forceps channel 168, are formed thin-walled by, for example, injection-molding a liquid crystal polymer, the scope with the forceps channel can be made much lighter in weight than a conventional one, so that the operator's labor for the operation can be saved.

Furthermore, the eyepiece section 164 can be formed by injection-molding a liquid crystal polymer. In this case, the high-frequency current leakage to the operator can be further securely prevented, and the scope can be reduced in weight. These effects can be also obtained with use of scopes of any other types.

Figure 19:
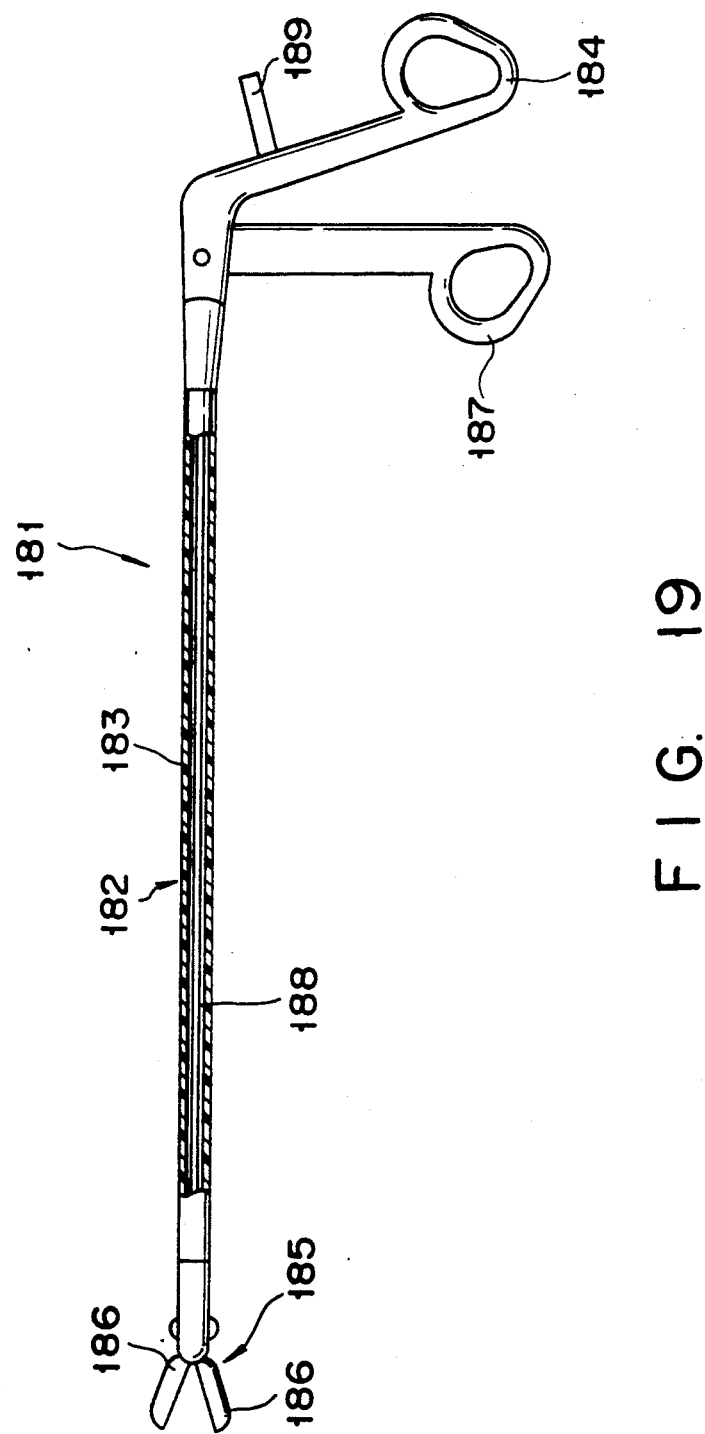
FIG. 19 is a cutaway side view of a biopsy forceps as a medical instrument according to a ninth embodiment of the invention.

FIG. 19 shows a biopsy forceps as a medical instrument according to a ninth embodiment of the present invention.

The biopsy forceps 181 comprises a rigid insertion section 182, which is composed of a rod 183 in the form of a thin-walled pipe obtained by injection-molding a liquid crystal polymer. A handle 184 and a treatment section 185 are attached to the proximal and distal ends, respectively, of the insertion section 182. The treatment section 185 is composed of a pair of cups 186. As an operating lever 187 attached to the handle 184 is moved back and forth, this motion is transmitted to the cups 186 by means of an operating wire 188 in the rod 183, so that the cups 186 open and close. A connector 189 for connecting a cord from a high-frequency power source (not shown) protrudes from the rear end of the handle 184. The respective surfaces of the handle 184 and the operating lever 187 are coated for insulation, and the cups 186, operating wire 188, and connector 189 are connected electrically to one another.

The following is a description of the biopsy forceps according to the ninth embodiment.

The biopsy forceps 181 is inserted into the body cavity with use of, for example, the thoracal mantle tube 41 shown in FIG. 9 as a guide. Then, the operating lever 187 is moved back and forth to cause the paired cups 186 to grasp the affected part. In this state, the cord from the high-frequency power source (not shown) is connected to the connector 189, and a high-frequency current is supplied to the cups 186. Thus, the tissue of the affected part can be burned off.

Conventionally, the rod of the insertion section is treated for insulation by, for example, coating a stainless-steel pipe with PTFE or the like. In the present embodiment, however, the rod 183 of the insertion section 182 is formed by injection-molding the liquid crystal polymer with high heat resistance into a thin-walled pipe, it has an insulating property. Therefore, the rod need not be coated for insulation, so that its diameter can be reduced so much, and an electric leakage attributable to peeling of the insulating coating can be prevented.

Since the rod 183 is formed of the liquid crystal polymer with high heat resistance, moreover, it cannot be distorted even if heat produced by the high-frequency current when the living body tissue is cauterized is transferred from the treatment section 185 to the rod 183.

In the biopsy forceps of the present embodiment, as in the other embodiments, the rod 183 and the handle 184 can be integrally formed with the connector 189 inserted therein, for example, by utilizing the high fluidity of the liquid crystal polymer. Further, the operating section 187 may be formed of a liquid crystal polymer.

Although the biopsy forceps has been described in connection with the present embodiment, the present invention may be also applied to forceps of other types, such as grip-type forceps, scissors-type forceps, etc., with the same results.

It is to be understood that the present invention is not limited to the embodiments and modifications described above, and that various changes and modifications may be effected therein by one skilled in the art without departing from the scope or spirit of the invention.

What is claimed is:

1. In a medical instrument having an insertion section including a tubular member that is insertable into a living body and an operating section which is operably connected to the tubular member of the insertion section for performing a medical activity through said insertion section;

the improvement comprising:

an injection molded insertion section tubular member formed entirely of an electrically insulating liquid crystal polymer, that increases in mechanical strength, in a unit area thereof, as a wall thickness of a wall of the insertion section tubular member decreases in thickness;

said wall of said insertion section tubular member being a unitary structure formed entirely of the liquid crystal polymer and including a core layer of the liquid crystal polymer sandwiched between first and second skin layers of the liquid crystal polymer;

said wall thickness of said wall of said insertion section tubular member being pre-selected to provide the insertion section tubular member with:

(a) a mechanical strength sufficient to withstand a bending force produced when the insertion section tubular member is inserted into the living body;

(b) a mechanical strength sufficient to prevent a collapse of the insertion section tubular member along a longitudinal axis thereof created by a pressure of the living body against a circumference of the insertion section tubular member;

(c) a small outside diameter relative to a diameter of a body cavity of the living body into which said insertion section tubular member is insertable, for reducing trauma to the living body upon insertion of the insertion section tubular member into the body cavity; and (d) an inside diameter that enables a plurality of medical apparatus respectively having a preset maximum diameter to be moved from the operating sections through the insertion section tubular member.

2. In the medical instrument according to claim 1, wherein:

said operating section has a tubular wall; and wherein both said operating section tubular outer wall and said at least an outer wall portion of said insertion section are both respectively integrally formed from a liquid crystal polymer.

3. In the medical instrument according to claim 1, wherein said insertion section tubular member includes a channel tube portion therein.

4. In the medical instrument according to claim 1, further comprising:

observation means attached to the operating section for viewing an inside portion of the living body; and guide means comprising said tubular member of the insertion section for introducing the observation means into the living body.

5. In the medical instrument according to claim 4, wherein said observation means comprises an optical observation scope attached to the operating section.

6. In the medical instrument according to claim 4, wherein said observation means comprises an electroscope.

7. In the medical instrument according to claim 1, further comprising:

cauterizing means for cauterizing at least some tissue in the living body, and guide means comprising the insertion section tubular member, for introducing the cauterizing means into the living body.

8. In the medical instrument according to claim 7, wherein said cauterizing means includes means for supplying a high-frequency current to the at least some tissue in the living body.

9. In the medical instrument according to claim 1, wherein the entire outer wall of said tubular member of the insertion section is formed of the liquid crystal polymer.

10. In the medical instrument according to claim 9, further comprising:

guide means for introducing a medicinal treatment means into the living body, said guide means comprising the tubular member of the insertion section.

11. In the medical instrument according to claim 1, further comprising:

treatment means attached to a distal end of the insertion section, said treatment means being connected to the operating section by said tubular member of said insertion section.

* * * * *